United States Patent [19]
Cooper et al.

[11] Patent Number: 5,479,929
[45] Date of Patent: Jan. 2, 1996

[54] DRIVE SYSTEM WITH A MULTITURN ROTARY STOP

[75] Inventors: Thomas G. Cooper, Menlo Park; David V. Adams, San Carlos; John W. Eaton, Palo Alto, all of Calif.

[73] Assignee: Acuson Corporation, Mountain View, Calif.

[21] Appl. No.: 267,594

[22] Filed: Jun. 27, 1994

[51] Int. Cl.$^6$ ....................................................... A61B 8/00
[52] U.S. Cl. ....................................................... 128/662.03
[58] Field of Search .................. 128/660.01, 660.08, 128/660.09, 660.10, 661.01, 662.03; 200/321; 33/542; 73/620, 627

[56] References Cited

U.S. PATENT DOCUMENTS

| | | | |
|---|---|---|---|
| 3,869,591 | 3/1975 | Piber | 200/321 |
| 4,341,120 | 7/1982 | Anderson . | |
| 4,649,925 | 3/1987 | Dow et al. . | |
| 4,663,858 | 5/1987 | Mahoney | 33/542 |
| 4,756,313 | 7/1988 | Terwilliger . | |
| 4,841,979 | 6/1989 | Dow et al. . | |
| 4,936,307 | 6/1990 | Saito et al. . | |
| 5,099,850 | 3/1992 | Matsui et al. . | |
| 5,159,931 | 11/1992 | Pini . | |
| 5,176,142 | 1/1993 | Mason . | |
| 5,181,514 | 1/1993 | Solomon et al. . | |
| 5,207,225 | 5/1993 | Oaks et al. . | |
| 5,320,104 | 6/1994 | Fearnside et al. . | |

OTHER PUBLICATIONS

Stock Drive Products, "Handbook of Design Components," Catalog D220, pp. T130–131 (1992).

*Primary Examiner*—George Manuel
*Attorney, Agent, or Firm*—Willian Brinks Hofer Gilson & Lione

[57] ABSTRACT

A drive system with a rotary stop for driving a rotatable load is provided having a motor, a rotary stop and a spring stop assembly for coupling the motor to the rotary stop. The spring stop assembly has a motor-driven gear coupled to a hub by a torsional spring. A position encoder may be attached to the motor. In addition, a drive shaft may be coupled to the motor and the multiturn rotary stop through the spring stop assembly.

22 Claims, 4 Drawing Sheets

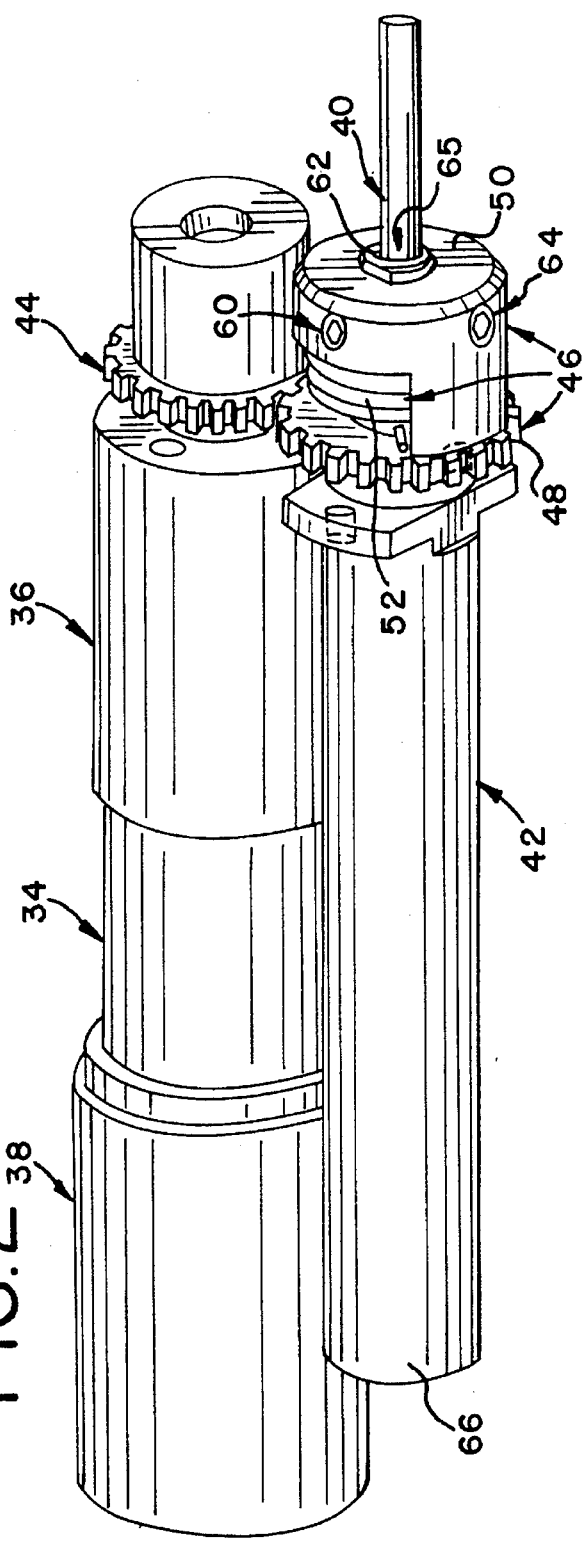
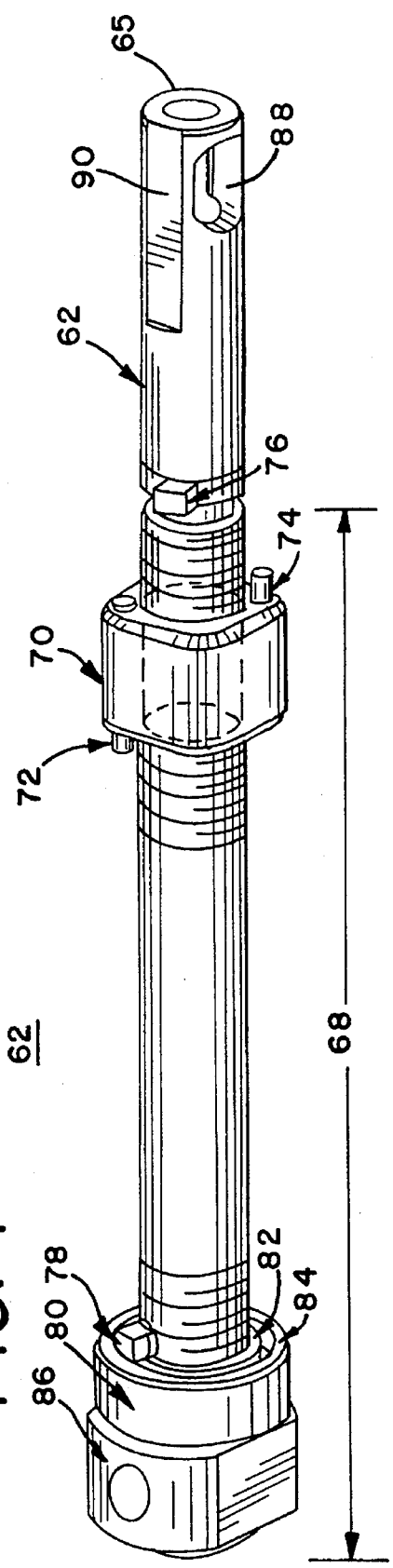

5,479,929

DRIVE SYSTEM WITH A MULTITURN ROTARY STOP

BACKGROUND OF THE INVENTION

The invention relates to ultrasonic imaging systems and, more particularly, to a drive system for an ultrasonic transducer probe electrically coupled to an ultrasonic imaging system.

The users of medical ultrasonic transducer probes, hereinafter referred to as sonographers, can obtain images of a region within a body by properly positioning a probe against the body. In order to obtain images having diagnostic value, the sonographer may have to physically manipulate the position of the probe by sliding, rotating, and tilting the probe. In one particularly challenging application, the sonographer positions a transducer scanhead at the tip of a transesophageal probe against the esophagus or stomach of a patient in order to obtain different fields of view of the heart.

Typically for this application, the transducer scanhead contains a number of acoustic transducer elements, which may be sequentially electrically excited by an ultrasound system to obtain an image in an object plane that is perpendicular to the scanhead and the transducer elements. It has been found desirable to rotate the transducer elements contained within the scanhead independently from the physical manipulation of the scanhead itself. By rotating the transducer elements, the object plane may be rotated in space about the axis of rotation of the transducer elements.

Devices are known that utilize a drive system to rotate an array of transducer elements. For example, an electric motor may be used to rotate the array of transducer elements with a position encoder, such as a potentiometer, coupled to the motor shaft to provide information on the position of the array of transducer elements. The position encoder may provide either an absolute or an incremental position of the rotatable array. The absolute position encoder can provide the actual position of the array at all times. The incremental position encoder, on the other hand, can provide the relative position of the array with respect to a particular reference position, such as the position of the array at the mime the ultrasound system is powered up.

A disadvantage of devices that utilize absolute position encoders is that such devices may be large and relatively heavy. In addition, analog absolute position encoders, such as potentiometers, may drift with temperature variations and time. It is desirable to minimize the size and weight of such drive systems as well as to provide position information that is stable over temperature variations and time.

A disadvantage of devices that utilize an incremental position encoder is that a rigid rotary stop may be utilized to establish a "home" or reference position. In an overtorque situation, the motor may drive the load into the stop at high speeds causing high shock loads and jamming the drive system.

Accordingly, it would be desirable to have an improved drive system for an ultrasonic probe.

SUMMARY OF THE INVENTION

According to a first aspect of the invention, a drive system for a rotatable load is provided having a motor, a rotary stop with a stop shaft disposed along a longitudinal axis of the rotary stop, a spring stop assembly for coupling the motor to the rotary stop, and a drive shaft for coupling the motor to the rotatable load.

According to a second aspect of the invention, a drive system for an ultrasonic probe is provided having a motor, a position encoder attached to the motor, a multiturn rotary stop, and a spring stop assembly. The spring stop assembly couples the motor to the multiturn rotary stop. The spring stop assembly has a motor-driven gear coupled to a hub by a torsional spring.

According to a third aspect of the invention, a drive system for an ultrasonic probe is provided having a motor, a rotatable stop shaft coupled to the motor, a traveling member with a cylindrical axial channel, and a pin fixed to the member. The rotatable stop shaft has a threaded portion and a stop adjacent to the threaded portion. The axial channel of the traveling member is threaded to mate with the threaded portion of the stop shaft, and the traveling member is positioned upon the threaded portion of the stop shaft. The pin fixed to the traveling member engages the stop when the member reaches an end of the threaded portion of the stop shaft.

BRIEF DESCRIPTION OF THE DRAWINGS

FIG. 2 is an enlarged view of a motor and a stop assembly as shown in the cut-away portion of FIG. 1.

FIG. 4 is an isometric view of a stop shaft for the stop assembly of FIG. 2.

DETAILED DESCRIPTION OF THE PRESENTLY PREFERRED EMBODIMENTS

Figure 1:
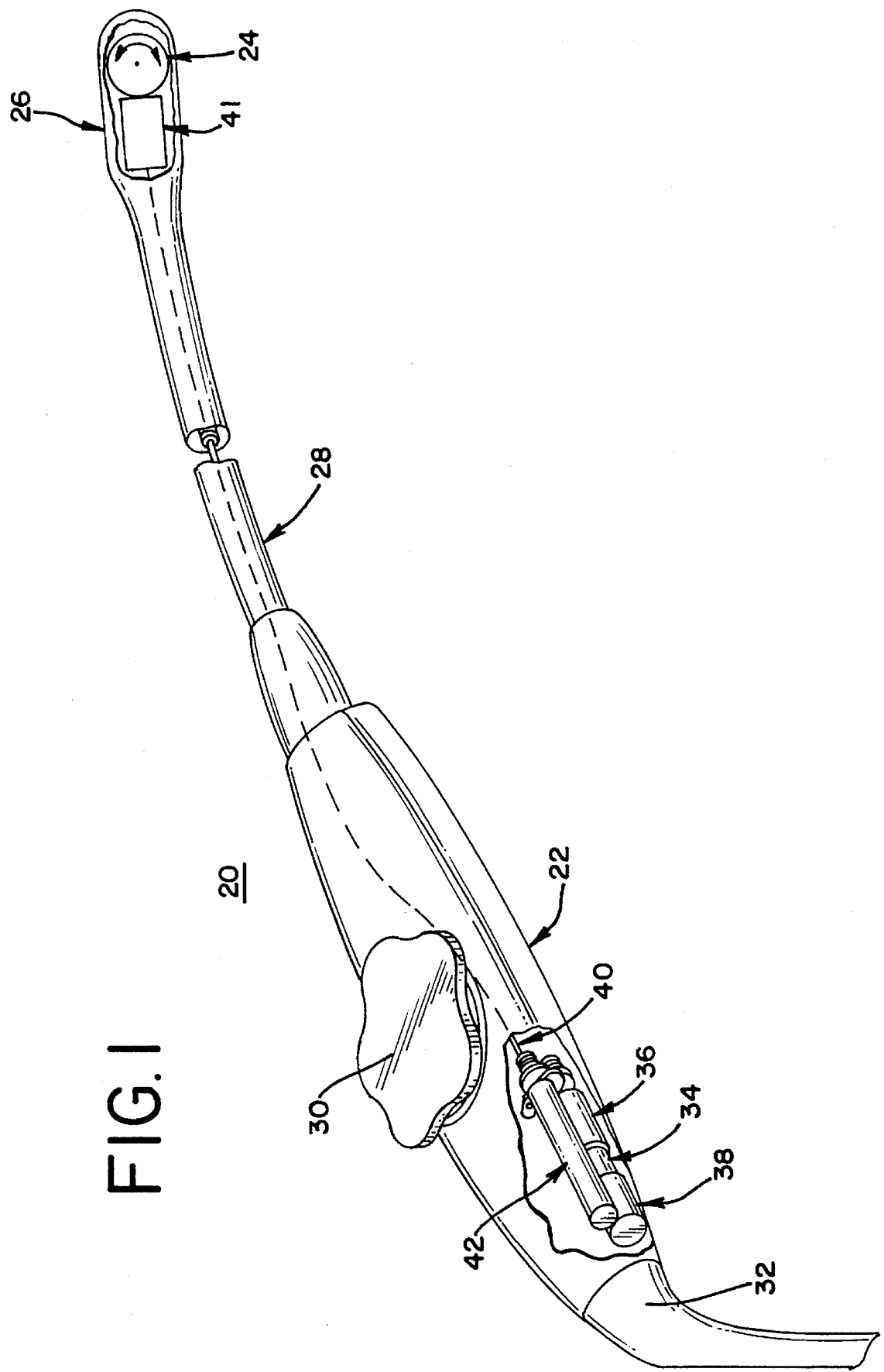
FIG. 1 is an isometric view of a transesophageal probe in accordance with the present invention.

FIG. 1 is a cut-away isometric view of a transesophageal probe 20 in accordance with the present invention. The probe 20 has a control housing 22 near its proximal end and a rotatable ultrasonic transducer array 24 mounted within a scanhead 26 at its distal end. A flexible endoscope 28 connects the scanhead 26 to the control housing 22. One or more control knobs 30 are mounted upon the control housing 22 to allow a sonographer to manipulate the position of the scanhead 26 against the esophagus or stomach of a patient. The control housing 22 is connected to a remote ultrasound system by a cable 32.

A drive system is provided for rotating the transducer array 24. As shown within the cut-away portion of FIG. 1, the control housing contains a motor 34, upon which is mounted a gear head 36 and a position encoder 38. The motor 34 and the position encoder 38 are electrically coupled to the remote ultrasound system through the cable 32. A suitable commercially available motor unit, including a gear head and an encoder, is available from Micro Mo of St. Petersburg, Fla., part no. 1331T-012S123+14/1, 3.71:1 X0437+ HEM1331T16+0437. For this unit, the gear head provides a reduction ratio of 3.71:1. This gear reduction allows the motor 34 to be run at efficient speeds and also allows the encoder 38, which is directly attached to the motor's shaft, to provide greater resolution on the motor shaft position. The position encoder 38 provided with the Micro Mo unit is an incremental magnetic encoder that has an output of sixty-four quadrature pulses per revolution of the motor shaft.

The gear head 36 is coupled to a drive shaft 40 through a multiturn rotary stop 42. The drive shaft 40 extends through the flexible endoscope 28 and projects into the scanhead 26, where it is coupled to the transducer array 24. Preferably, the drive shaft 40 is flexible so that it may move with flexible endoscope as the sonographer manipulates the probe 20.

Due to the length of the drive shaft 40 and the mass of the transducer array 24, the drive shaft 40 may torsionally deflect in response to torque applied to the drive shaft 40 at the point where it is coupled to the transducer array 24. Thus, a speed reducer 41 couples the drive shaft 40 to the transducer array 24. The speed reducer 41 allows the drive shaft 40 to run at high speeds with low torque. As a result, the speed reducer 41 minimizes positional error due to torsional deflection of the drive shaft 40. Preferably, the speed reducer 41 provides a 121:1 gear reduction so that the drive shaft 40 rotates 60.5 times for one-half turn (180°) of the transducer array 24.

An enlarged view of the motor 34 and the multiturn rotary stop 42 assembly is shown in FIG. 2. The gear head 36 drives a motor gear 44, which in turn drives a spring stop assembly 46. The spring stop assembly 46 is shown in FIGS. 3A to 3F. As shown in FIG. 3A, the spring stop assembly 46 has a gear 48 coupled to a hub 50 by a preloaded torsional spring 52. The gear 48 has a cylindrical channel 54 through its and a curved flange 56, as best shown in FIG. 3B, which projects toward the hub 50 (not shown in FIG. 3B). The torsional spring 52 is preloaded by positioning it around the cylindrical channel 54 with the ends 52a and 52b of the torsional spring being separated by the flange 56.

Figure 3C:
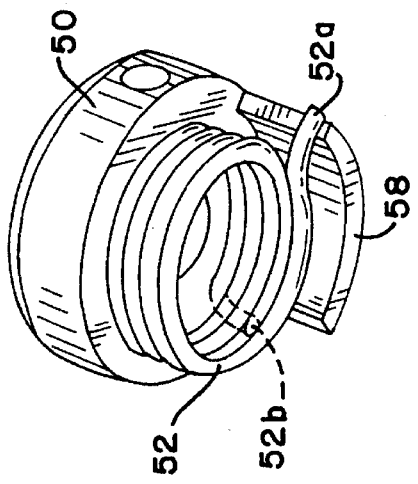
FIGS. 3A through 3F are views of a spring stop assembly from the stop assembly of FIG. 2.
Figure 3F:
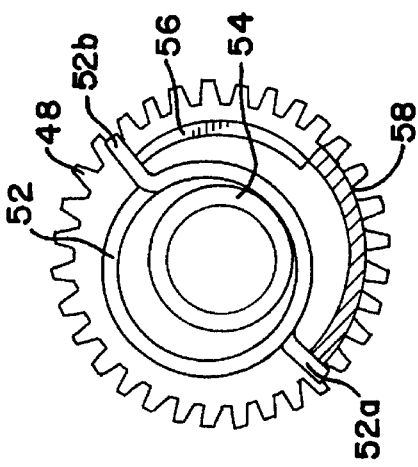
Figure 3B:
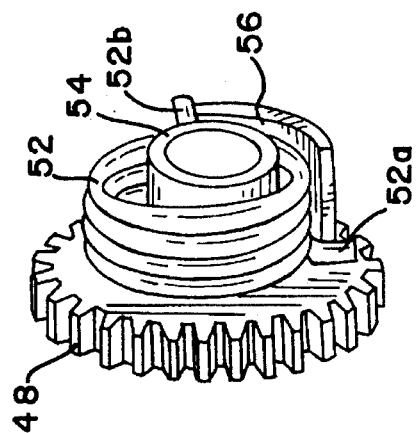
Figure 3E:
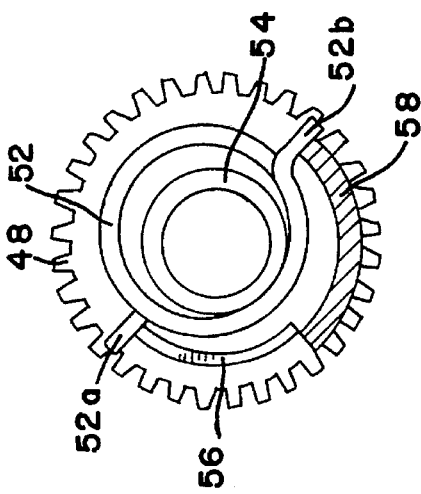
Figure 3A:
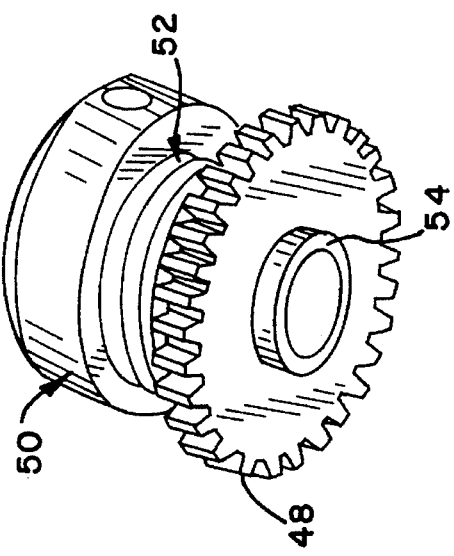
Figure 3D:
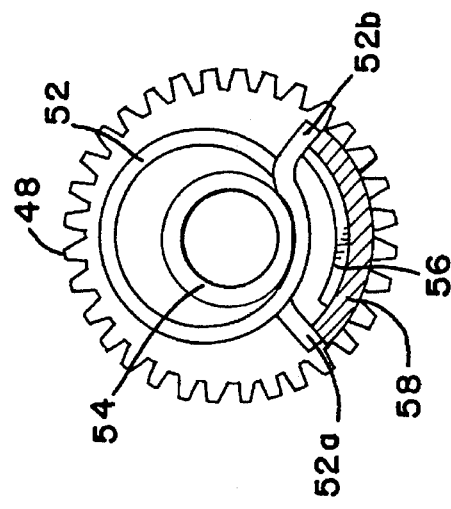

FIG. 3C shows the spring stop assembly 46 with the gear 48 removed. The hub 50 has a curved flange 58, which projects toward the gear 48 (not shown in FIG. 3C). The ends 52a and 52b of the torsional spring 52 are separated by the flange 58. As is best shown in FIG. 3D, the flange 58 and the flange 56 are curved and concentrically positioned so that they mate, thereby allowing the gear 48 to rotate relative to the hub 50, against the resistance of the torsional spring 52, without interference between the flanges 56 and 58.

A suitable torsional spring for this application is available from Associated Spring of Corry, Pa., part no. T-028-180-203-R, which provides a specified torque of 0.515 lb.-in. at 180° deflection. This standard spring is modified for this application by forming hooks on the ends of the spring as shown in FIGS. 3B through 3F so that the spring may be preloaded by placing the ends 52a and 52b over the flanges 56 and 58. Preferably, the flanges 56 and 58 are sized to preload the torsional spring 52 by 4 oz.-in. (approximately 90°).

Referring again to FIG. 2, the spring stop assembly 46 is mounted to the rotary stop 42. A set screw 60 secures the hub 50 of the spring stop assembly 46 to a stop shaft 62, shown in FIG. 4, which is located along the longitudinal axis of the rotary stop 42. A second set screw 64 secures the hub 50 to the drive shaft 40. The stop shaft 62 projects along the longitudinal axis of the rotary stop 42, through the cylindrical channel 52 in the gear 48, and through the circular opening 55 in the hub 50. The end of the stop shaft 62 has an opening 65 for receiving the drive shaft 40. A stop housing 66 encases the distal portion of the stop shaft 62.

FIG. 4 is an isometric view of the stop shaft 62. The stop shaft 62 has a threaded portion 68, which carries a traveling nut 70. Two pins 72 and 74 are pressed into the nut 70. The pins 72 and 74 are aligned parallel to the stop shaft 62, with the pin 72 projecting toward the distal end of the stop shaft and the pin 74 projecting toward the proximal end. A stop 76 located adjacent to the threaded portion 68 projects from the stop shale 62 in a direction that is transverse to the longitudinal axis of the stop shaft 62.

Near the distal end of the stop shaft 62, a stop 78 is fitted in a hole that is cross drilled in the stop shaft 62. A bearing 80 having an inner race 82 and an outer race 84 is fitted to the stop 78 so that the inner diameter of the outer race 84 prevents the stop 78 from falling through the hole in the stop shaft 62. A shaft clamp 86 threads on to the stop shaft 62 to clamp the inner race 82 of the bearing 80. The stops 76 and 78 limit the travel of the traveling nut 70 of the rotary stop 42.

Because the drive shaft 40 and the stop shaft 62 attached thereto rotate 60.5 times in order to rotate the transducer array 24 180°, the threaded portion 68 is preferably sized so that the stop shaft 62 rotates 62.5 times as the traveling nut 70 moves from one stop, such as 78, to the other stop, such as 76. Preferably, a 0.020 pitch screw thread is used on the threaded portion 68 of the stop shaft 62. A larger pitch screw thread will increase the physical length of the rotary stop 42, while a smaller pitch screw thread increase the axial force on the traveling nut 70. The rotary stop 42 may be approximately 0.335 in. in diameter and 2 in. in length so that it fits comfortably within the control housing 22.

The stop shaft 62 has a hole 88 located near its proximal end. The hole 88 allows the set screw 64 in the hub 50 to clamp the drive shaft 40, which is inserted into the opening 65 in the end of the stop shaft 62. Preferably, the stop shaft has a flattened area 90 for securely seating the set screw 60, which secures the hub 50 of the spring stop assembly 46 to the stop shaft 62.

Figure 5A:
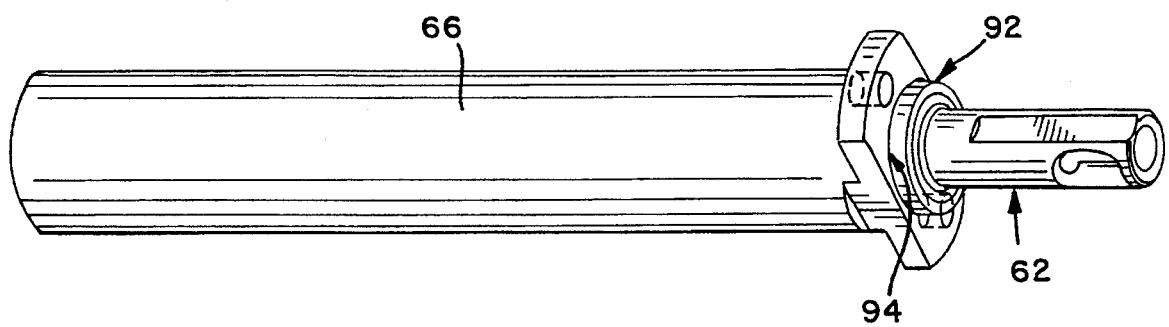
FIGS. 5A and 5B are views of the stop assembly of FIG. 2 with subassemblies removed.

FIG. 5A is an isometric view of the rotary stop 42 in which the spring stop assembly 46 has been removed for clarity. A bearing 92 supports the stop shaft 62 for rotation. The bearing 92 is fixed to he stop housing 66 at a circular opening 94 therein.

Figure 5B:
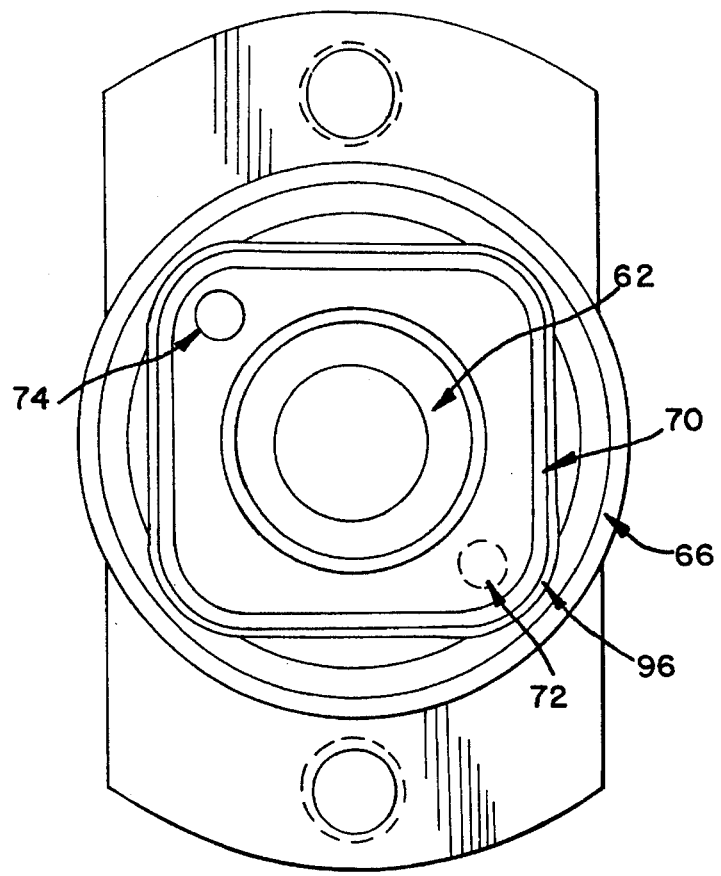

FIG. 5B is an end view of the proximal end of the rotary stop 42 in which the spring stop assembly 46 and the bearing 92 have been removed. The stop shaft 62 is centered within the stop housing 66. The stop housing 66 has an internal chamber 96, which has a square cross section. The square shape of the internal chamber 96 prevents the traveling nut 70 from rotating. The pin 74 is also shown. Alternative nut 70 and chamber 96 configurations may be used to prevent the nut 70 from rotating.

An alternative drive system may include a gear reduction between the drive shaft 40 and the multiturn rotary stop 42, although a drive system without gear reduction between the drive shaft 40 and the rotary stop 42 is preferred. If gear reduction is used between the drive shaft 40 and the multiturn rotary stop 42, then the number of turns that the stop shaft 62 makes between the stops 76 and 78 is reduced. However, the torque that is applied to the stop shaft 62 is multiplied by the reduction ratio. Accordingly, the rotary stop must be constructed to withstand the amplified torque, which increases the size and weight of the rotary stop.

In operation, the remote ultrasound system provides motor control signals to the motor 34 through the cable 32, and the position encoder 38 provides the changes in the position of the motor's shaft to the ultrasound system. From the gear ratios of the drive system between the motor 34 and the ultrasonic transducer array 24, the change in position of the array 24 can be determined from the change in position of the motor shaft. Therefore, once the absolute position of the array 24 is known, the incremental position encoder 38 allows the ultrasound system to track the absolute position of the array 24 as it is rotated by the drive system.

The absolute position of the array 24 can be initially determined using the multiturn rotary stop 42. Upon power up of the ultrasound system, the system causes the motor 34 to rotate in one direction, which in turn causes the spring stop assembly 46 to rotate. Because the hub 50 of the spring stop assembly 46 is fixed to the stop shaft 62 and the drive shaft 40, the stop shaft 62, the drive shaft 40 and the array 24 also rotate.

As the stop shaft 62 rotates, the traveling nut 70 moves toward an end of the threaded portion 68 of the stop shaft 62. Due to the fine pitch screw thread on the stop shaft 62, the stop shaft 62 places a large axial force on the traveling nut 70. Eventually, depending on the direction of rotation, one of the pins 72 or 74 on the traveling nut will strike a stop 78 or 76. Because the stops 78 and 76 rotate with the stop shaft 62, they will strike the pins 72 and 74 tangentially, thereby stopping the traveling nut 70 and absorbing the large axial force on the nut 70, without jamming of the nut 70 against the stops 78 and 76.

Preferably, the pins 72 and 74 are positioned so that on the turn of the stop shaft 62 before the pins 72 and 74 engage the stops 78 and 76, the pins 72 and 74 miss striking the stops 78 and 76 by 0.006 inches, and on the final turn of the stop shaft 62, the pins 72 and 74 overlap the stops 78 and 76 by 0.014 inches. Because the pins 72 and 74 are press fitted, they may be adjusted after the traveling nut 70 is threaded onto the stop shaft 62 to obtain the desired clearance and overlap with respect to the stops 76 and 78. As an alternative to press pins 72 and 74, the nut 70 may be formed with integral pins, which may be machined to the appropriate length after the nut 70 is threaded onto the stop shaft 62.

When the motor 34, through the gear head 36, applies a torque that is less than the preload of the torsional spring 52, and the pins 72 and 74 strike the stops 78 and 76, respectively, then the stop shaft 62, the drive shaft 40, the array 24, the spring stop assembly 46 and the motor 34 stop rotating. As a result, the position encoder 38 stops indicating a change in position of the motor shaft even though the motor control signal from the ultrasound system has not changed. In this condition, the ultrasound system knows that the transducer array 24 has reached its "home" or reference position, and the absolute position of the array 24 is known for as long as the system remains powered.

The spring stop assembly 46 protects the drive system and the transducer array 24 from high shock loads that can be generated when the pins 72 and 74 of the traveling nut 70 strike the stops 76 and 78. Under normal operating conditions, the motor 34 supplies less than 2 oz.-in. of torque and the spring stop assembly 46 is rigid, that is, the preloaded torsional spring 52 causes the spring stop assembly 46 to rotate and stop without any relative motion between the gear 48 and the hub 50.

If, on the other hand, the motor 34 supplies greater than 4 oz.-in. of torque, which is an overtorque condition, then the torsional spring 52 allows the gear 48 to deflect relative to the hub 50. For example, if the motor 34 drives the pin 74 of the traveling nut 70 into the stop 76 at greater than 4 oz.-in. of torque, then the spring stop assembly 46 absorbs the excessive shock by allowing the gear 48 to deflect while the hub 50, the drive shaft 40, and the array 24 remain stationary. FIG. 3E shows the spring stop assembly 46 with the hub 50 removed and the gear 48 deflected clockwise by 90 degrees; a condition in which the torsional spring 52 has absorbed 8 oz.-in. of torque. In addition, because the torsional spring 52 returns the gear 48 by the amount of the deflection, the position encoder 38 remains accurate in indicating the position of the array 24. It should be noted that the spring stop assembly 46 allows the excessive shock to be absorbed, thereby preventing damage to the torsional spring 52, the motor gear head 36, and the components of the rotary stop 42, whether the shaft of the motor 36 is turning clockwise or counterclockwise. FIG. 3F shows the counterclockwise analog to FIG. 3E.

Regardless of whether the spring stop assembly 46 is rigid or is deflected to absorb excess torque, the rotary stop 42 and the transducer array 24 stop rotating when the pins 72 and 74 on the traveling nut 70 strike the stops 78 and 76. Therefore, it is not necessary to allow for overtravel of the rotating structures.

Although the drive system described herein is operable within a transesophageal probe 20, it is understood that the drive system may be used to drive other rotatable loads. It is intended that the foregoing detailed description be regarded as illustrative rather than limiting and that it is understood that the following claims, including all equivalents, are intended to define the scope of the invention.

We claim:

1. A drive system for an ultrasonic probe, comprising:

a motor;

a position encoder attached to the motor;

a multiturn rotary stop having a threaded portion; and a spring stop assembly coupling the motor to the multiturn rotary stop, wherein the spring stop assembly comprises a motor-driven gear coupled to a hub by a torsional spring, and wherein the hub is fixed to the multiturn rotary stop.

2. A drive system as claimed in claim 1, wherein the position encoder is a magnetic quadrature encoder for providing incremental position information.

3. A drive system as claimed in claim 1, wherein the multiturn rotary stop comprises a traveling nut mounted upon the threaded portion of the multiturn rotary stop, the traveling nut having at least one pin extending therefrom.

4. A drive system as claimed in claim 3, wherein the pin strikes a stop tangentially.

5. A drive system for an ultrasonic probe, comprising:

a rotatable gear having a cylindrical channel defining an axis of rotation;

means for rotating the gear; and a hub coupled to the rotatable gear by a torsional spring positioned around the cylindrical channel, wherein the torsional spring allows the gear to rotate relative to the hub upon application of a predetermined torque to the gear or the hub.

6. A drive system as claimed in claim 5, wherein the rotating means comprises an electric motor.

7. A drive system as claimed in Claim 5, further comprising a flexible drive shaft fixed to the hub.

8. A drive system as claimed in Claim 7 further comprising a rotary stop having a stop shaft, wherein the stop shaft is fixed to the flexible drive shaft.

9. A drive system as claimed in Claim 8, wherein the stop shaft extends through the cylindrical channel and the hub, whereby the stop shafts forms an axis of rotation for the gear and the hub.

10. A drive system as claimed in Claim 8, wherein the rotary stop further comprises a traveling nut having a pin extending from the nut in a direction parallel to the stop shaft, and a stop fixed to the stop shaft and positioned to engage the pin.

11. A drive system as claimed in Claim 1, further comprising:

a drive shaft connected to the spring stop assembly;

a speed reducer coupled to the drive shaft; and an array of ultrasonic transducer elements coupled to the speed reducer.

12. A drive system as claimed in claim 11, wherein the drive shaft is attached to the hub.

13. A drive system as claimed in claim 12, wherein the drive shaft is flexible.

14. A drive system for an ultrasonic probe, comprising:

a motor having a shaft;

a rotatable stop shaft mechanically coupled to the shaft of the motor, wherein the rotatable stop shaft has a threaded portion and a stop adjacent to the threaded portion;

a traveling member having a cylindrical axial channel, wherein the channel is threaded to mate with the threaded portion of the stop shaft, the member being positioned upon the threaded portion of the stop shaft; and a pin extending from the traveling member for engaging the stop when the traveling member reaches an end of the threaded portion of the stop shaft.

15. A drive system as claimed in claim 14, further comprising a housing for the threaded portion of the stop shaft, wherein the housing is shaped to prevent the traveling member from rotating.

16. A drive system as claimed in claim 15, wherein the pin extends from the traveling member in a direction that is parallel to a longitudinal axis of the stop shaft.

17. A drive system for a rotatable load, comprising:

a motor having a shaft;

a mechanical rotary stop having a threaded stop shaft disposed along a longitudinal axis of the rotary stop;

a spring stop assembly comprising a gear having a cylindrical channel, the spring stop assembly coupling the motor to the rotary stop, wherein the stop shafts extends into the cylindrical channel; and means for coupling the shaft of the motor to the rotatable load.

18. A drive system as claimed in claim 17, wherein the coupling means comprises a drive shaft.

19. A drive system as claimed in claim 17, wherein the spring stop assembly further comprises a hub mounted to the stop shaft, and a torsional spring coupling the gear to the hub.

20. A drive system as claimed in claim 19, wherein the torsional spring is preloaded, whereby the gear and the hub of the spring stop assemble rotate.

21. A drive system as claimed in claim 20, wherein the coupling means comprises a flexible drive shaft attached at a first end of the hub, wherein a second end of the flexible drive shaft is coupled to the rotatable load.

22. A method of determining a position of a rotatable load, comprising the steps of:

providing a motor coupled to a position encoder and a spring stop assembly;

providing a rotary stop and a drive shaft coupled to the rotatable load, wherein the drive shaft is coupled to the rotary stop and the rotary stop is coupled to the spring stop assembly;

rotating the drive shaft by driving the spring stop assembly with the motor until the rotary stop reaches a travel limit; and monitoring changes in the position of the rotatable load after the rotary stop reaches the travel limit.

\* \* \* \* \*